United States Patent
Quintana et al.

(10) Patent No.: US 12,097,145 B2
(45) Date of Patent: *Sep. 24, 2024

(54) VENTED MULTI-DOSE OCULAR FLUID DELIVERY SYSTEM

(71) Applicant: Bausch + Lomb Ireland Limited, Dublin (IE)

(72) Inventors: Reynaldo Quintana, Menlo Park, CA (US); Yehuda Ivri, Newport Coast, CA (US); Daniel V. Palanker, Sunnyvale, CA (US)

(73) Assignee: BAUSCH + LOMB IRELAND LIMITED, Dublin (IE)

( * ) Notice: Subject to any disclaimer, the term of this patent is extended or adjusted under 35 U.S.C. 154(b) by 676 days.

This patent is subject to a terminal disclaimer.

(21) Appl. No.: 17/127,584

(22) Filed: Dec. 18, 2020

(65) Prior Publication Data

US 2021/0137732 A1    May 13, 2021

Related U.S. Application Data

(63) Continuation-in-part of application No. 16/811,879, filed on Mar. 6, 2020, now Pat. No. 11,679,028.
(Continued)

(51) Int. Cl.
*A61F 9/00*    (2006.01)
*A61J 1/14*    (2023.01)

(52) U.S. Cl.
CPC .......... *A61F 9/0008* (2013.01); *A61J 1/1443* (2013.01)

(58) Field of Classification Search
CPC ..... A61F 9/0026; A61F 9/0008; A45D 34/00; A61M 11/005; A61M 15/0028;
(Continued)

(56) References Cited

U.S. PATENT DOCUMENTS 3,640,274 A    2/1972 Costello
3,779,245 A    12/1973 Windsor
(Continued)

FOREIGN PATENT DOCUMENTS

CN    103118642 A    5/2013
CN    104146816 A    11/2014
(Continued)

OTHER PUBLICATIONS

Abidi et al., "Lifilegrast: A Novel Drug for Treatment of Dry Eye Disease", Journal of Pharmacology and Pharmacotherapy, 2016, vol. 7, pp. 194-198.
(Continued)

*Primary Examiner* — Kai H Weng
*Assistant Examiner* — Alessandro R Del Priore
(74) *Attorney, Agent, or Firm* — Perilla Knox & Hildebrandt LLP; Bradley K. Groff; Stephanie L. Davy-Jow

(57) ABSTRACT

A device for delivery of a precise amount of pharmaceutical fluid to the eye is provided. The device includes an ampoule for storing a liquid and an aperture through which the liquid is discharged. The device further includes a vibrating membrane that includes a needle which protrudes from the membrane and extends to the aperture to form a needle valve. The needle valve provides hermetic closure of the aperture to enable preservative-free storage of the pharmaceutical fluid in the device. The system further includes an electromagnetic transducer to shift the membrane back and forth in order to discharge liquid through the nozzle. Finally, the system further includes a vent to permit air to enter the ampoule as fluid is ejected from the ampoule. Preferably this vent includes a filter to prevent ingress of microbes or other contaminants to the ampoule.

13 Claims, 6 Drawing Sheets

Related U.S. Application Data

(60) Provisional application No. 63/049,582, filed on Jul. 8, 2020, provisional application No. 63/049,110, filed on Jul. 7, 2020, provisional application No. 63/011,800, filed on Apr. 17, 2020, provisional application No. 62/951,903, filed on Dec. 20, 2019, provisional application No. 62/814,773, filed on Mar. 6, 2019.

(58) Field of Classification Search
CPC ... B05B 11/007; B05B 11/3032; B05B 17/04; B05B 17/0607; B05B 17/0623; B05B 17/0646
See application file for complete search history.

(56) References Cited

U.S. PATENT DOCUMENTS

| | | | |
|---|---|---|---|
| 3,812,854 A | 5/1974 | Michaels et al. | |
| 3,861,386 A | 1/1975 | Harris et al. | |
| 3,934,585 A | 1/1976 | Maurice | |
| 3,970,250 A | 7/1976 | Drews | |
| 3,976,072 A | 8/1976 | Walker | |
| 4,159,803 A | 7/1979 | Cameto et al. | |
| 4,300,546 A | 11/1981 | Kruber | |
| 4,334,531 A | 6/1982 | Reichl et al. | |
| 4,338,576 A | 7/1982 | Takahashi et al. | |
| 4,344,744 A | 8/1982 | Schuster et al. | |
| 4,352,459 A | 10/1982 | Berger et al. | |
| 4,465,234 A | 8/1984 | Maehara et al. | |
| 4,632,311 A | 12/1986 | Nakane et al. | |
| 4,655,393 A | 4/1987 | Berger | |
| 4,793,339 A | 12/1988 | Matsumoto et al. | |
| 4,850,534 A | 7/1989 | Takahashi et al. | |
| 4,882,150 A | 11/1989 | Kaufman | |
| 4,952,581 A | 8/1990 | Bito et al. | |
| 4,961,345 A | 10/1990 | Tsuruoka et al. | |
| 4,976,259 A | 12/1990 | Higson et al. | |
| 4,981,625 A | 1/1991 | Rhim et al. | |
| 5,025,957 A * | 6/1991 | Ranalletta | B05B 11/047 222/189.09 |
| 5,171,306 A | 12/1992 | Vo | |
| 5,232,363 A | 8/1993 | Meller | |
| 5,368,582 A | 11/1994 | Bertera | |
| 5,370,317 A | 12/1994 | Weston | |
| 5,487,378 A | 1/1996 | Robertson et al. | |
| 5,549,249 A | 8/1996 | Foster et al. | |
| 5,624,057 A | 4/1997 | Lifshey | |
| 5,627,611 A | 5/1997 | Scheiner | |
| 5,630,793 A | 5/1997 | Rowe | |
| 5,657,926 A | 8/1997 | Toda | |
| 5,692,651 A | 12/1997 | Fuchs | |
| 5,811,443 A | 9/1998 | DeSantis, Jr. et al. | |
| 5,828,394 A | 10/1998 | Khuri-Yakub et al. | |
| 5,938,117 A | 8/1999 | Ivri | |
| 5,958,342 A | 9/1999 | Gamble et al. | |
| 5,960,224 A | 9/1999 | Sanada et al. | |
| 6,024,717 A | 2/2000 | Ball et al. | |
| 6,062,212 A | 5/2000 | Davison et al. | |
| 6,065,623 A | 5/2000 | Hierzer et al. | |
| 6,095,376 A | 8/2000 | Hennemann et al. | |
| 6,196,218 B1 | 3/2001 | Voges | |
| 6,232,129 B1 | 5/2001 | Wiktor | |
| 6,273,092 B1 | 8/2001 | Nolan | |
| 6,302,101 B1 | 10/2001 | Py | |
| 6,419,663 B2 * | 7/2002 | Harrold | B05B 11/1091 604/298 |
| 6,467,476 B1 | 10/2002 | Ivri et al. | |
| RE38,077 E | 4/2003 | Cohen et al. | |
| 6,543,442 B2 | 4/2003 | Gonda et al. | |
| 6,629,646 B1 | 10/2003 | Ivri | |
| 6,730,066 B1 | 5/2004 | Bennwik et al. | |
| 6,758,837 B2 | 7/2004 | Péclat et al. | |
| 6,869,275 B2 | 3/2005 | Dante et al. | |
| 7,066,398 B2 | 6/2006 | Borland et al. | |
| 7,105,357 B1 | 9/2006 | Kalkum et al. | |
| 7,201,732 B2 | 4/2007 | Anderson et al. | |
| 7,314,938 B2 | 1/2008 | Shen et al. | |
| 7,571,722 B2 | 8/2009 | Wuttke et al. | |
| 7,745,460 B2 | 6/2010 | Shen et al. | |
| 7,790,743 B2 | 9/2010 | Shen et al. | |
| 7,874,467 B2 | 1/2011 | Pardes | |
| 7,883,031 B2 | 2/2011 | Collins, Jr. et al. | |
| 7,928,122 B2 | 4/2011 | Shen et al. | |
| 8,012,136 B2 | 9/2011 | Collins, Jr. et al. | |
| 8,048,047 B2 | 11/2011 | Domash | |
| 8,056,766 B2 | 11/2011 | Grevin | |
| 8,128,606 B2 | 3/2012 | Anderson et al. | |
| 8,133,210 B2 | 3/2012 | Al-Abdulla et al. | |
| 8,144,399 B2 | 3/2012 | Steenblik et al. | |
| 8,168,655 B2 | 5/2012 | Gadek et al. | |
| 8,273,307 B2 | 9/2012 | Eickhoff et al. | |
| 8,367,701 B2 | 2/2013 | Burnier et al. | |
| 8,398,001 B2 | 3/2013 | Borland et al. | |
| 8,435,544 B2 | 5/2013 | Mitra et al. | |
| 8,544,462 B2 | 10/2013 | Papania et al. | |
| 8,545,463 B2 | 10/2013 | Collins, Jr. et al. | |
| 8,592,450 B2 | 11/2013 | Gadek et al. | |
| 8,629,111 B2 | 1/2014 | Acheampong et al. | |
| 8,633,162 B2 | 1/2014 | Acheampong et al. | |
| 8,642,556 B2 | 2/2014 | Acheampong et al. | |
| 8,648,048 B2 | 2/2014 | Acheampong et al. | |
| 8,684,980 B2 | 4/2014 | Hunter et al. | |
| 8,685,930 B2 | 4/2014 | Acheampong et al. | |
| 8,722,728 B2 | 5/2014 | Wong et al. | |
| 8,733,935 B2 | 5/2014 | Ballou, Jr. et al. | |
| 8,863,998 B2 | 10/2014 | Painchaud et al. | |
| 8,927,574 B2 | 1/2015 | Burnier | |
| 8,927,921 B1 | 1/2015 | Nelms et al. | |
| 8,936,021 B2 | 1/2015 | Collins, Jr. | |
| 9,039,666 B2 | 5/2015 | Voss et al. | |
| 9,068,566 B2 | 6/2015 | Ivri | |
| 9,085,553 B2 | 7/2015 | Zeller et al. | |
| 9,087,145 B2 | 7/2015 | Ballou, Jr. et al. | |
| 9,186,690 B2 | 11/2015 | Scanlon et al. | |
| 9,216,174 B2 | 12/2015 | Shen et al. | |
| 9,238,532 B2 | 1/2016 | Decock et al. | |
| 9,248,191 B2 | 2/2016 | Acheampong et al. | |
| 9,353,088 B2 | 5/2016 | Burnier | |
| 9,447,077 B2 | 9/2016 | Burnier et al. | |
| 9,597,230 B2 | 3/2017 | Haffner et al. | |
| 9,676,525 B2 | 6/2017 | Greiner-Perth et al. | |
| 9,700,686 B2 | 7/2017 | Gavini et al. | |
| 9,801,757 B2 | 10/2017 | Voss et al. | |
| 9,808,825 B2 | 11/2017 | Aguilar | |
| 9,867,933 B2 | 1/2018 | Pardes et al. | |
| 9,890,141 B2 | 2/2018 | Burnier | |
| 10,073,949 B2 | 9/2018 | Ballou, Jr. et al. | |
| 10,105,720 B2 | 10/2018 | Decock et al. | |
| 10,124,000 B2 | 11/2018 | Shen et al. | |
| 10,154,923 B2 | 12/2018 | Hunter et al. | |
| 10,174,017 B2 | 1/2019 | deLong et al. | |
| 10,314,740 B2 | 6/2019 | Kraft | |
| 10,624,781 B2 | 4/2020 | Ivri | |
| 11,278,448 B2 | 3/2022 | Palanker et al. | |
| 2001/0035184 A1 | 11/2001 | Schuler et al. | |
| 2001/0036424 A1 | 11/2001 | Takahashi et al. | |
| 2001/0036449 A1 | 11/2001 | Garst | |
| 2002/0078947 A1 | 6/2002 | Gumaste | |
| 2002/0124843 A1 | 9/2002 | Skiba et al. | |
| 2002/0158196 A1 | 10/2002 | Berggren et al. | |
| 2002/0161344 A1 | 10/2002 | Peclat et al. | |
| 2002/0185125 A1 | 12/2002 | Klimowicz et al. | |
| 2002/0190079 A1 | 12/2002 | Hamamoto | |
| 2003/0052573 A1 | 3/2003 | Wischnewskiy | |
| 2003/0065294 A1 | 4/2003 | Pickup et al. | |
| 2003/0071071 A1 | 4/2003 | Garcia et al. | |
| 2003/0140921 A1 | 7/2003 | Smith et al. | |
| 2004/0039355 A1 | 2/2004 | Gonzalez et al. | |
| 2004/0050861 A1 | 3/2004 | Lisec et al. | |
| 2004/0138630 A1 | 7/2004 | Al-Abdulla et al. | |
| 2004/0163645 A1 | 8/2004 | Connelly et al. | |
| 2004/0173642 A1 | 9/2004 | Clifford et al. | |
| 2004/0204674 A1 | 10/2004 | Anderson et al. | |

(56) References Cited

U.S. PATENT DOCUMENTS

| | | |
|---|---|---|
| 2004/0215157 A1 | 10/2004 | Peclat et al. |
| 2004/0256487 A1 | 12/2004 | Collins, Jr. et al. |
| 2004/0263567 A1 | 12/2004 | Hess et al. |
| 2005/0001981 A1 | 1/2005 | Anderson et al. |
| 2005/0006417 A1 | 1/2005 | Nicol et al. |
| 2005/0107832 A1 | 5/2005 | Bernabei |
| 2005/0172962 A1 | 8/2005 | Gumaste et al. |
| 2005/0207917 A1 | 9/2005 | Koerner et al. |
| 2005/0240162 A1 | 10/2005 | Chen et al. |
| 2005/0261641 A1 | 11/2005 | Warchol et al. |
| 2006/0065677 A1 | 3/2006 | Py et al. |
| 2006/0069358 A1 | 3/2006 | Gerondale |
| 2006/0147313 A1 | 7/2006 | Zengerle et al. |
| 2006/0210604 A1 | 9/2006 | Dadey et al. |
| 2007/0051362 A1 | 3/2007 | Sullivan et al. |
| 2007/0088267 A1 | 4/2007 | Shekalim |
| 2007/0088268 A1 | 4/2007 | Edwards |
| 2007/0102455 A1 | 5/2007 | Stark |
| 2007/0119969 A1 | 5/2007 | Collins, Jr. et al. |
| 2007/0195151 A1 | 8/2007 | Anderson et al. |
| 2007/0268340 A1 | 11/2007 | Dacquay et al. |
| 2007/0295332 A1 | 12/2007 | Ziegler et al. |
| 2008/0039807 A1 | 2/2008 | Pine |
| 2008/0202514 A1 | 8/2008 | Kriksunov et al. |
| 2008/0214940 A1 | 9/2008 | Benaron et al. |
| 2008/0233053 A1 | 9/2008 | Gross et al. |
| 2008/0247264 A1 | 10/2008 | Gabl et al. |
| 2008/0257911 A1 | 10/2008 | Choi et al. |
| 2009/0060793 A1 | 3/2009 | Eickhoff et al. |
| 2009/0114742 A1 | 5/2009 | Collins, Jr. |
| 2009/0134235 A1 | 5/2009 | Ivri |
| 2009/0182291 A1 | 7/2009 | Eilat |
| 2009/0192443 A1 | 7/2009 | Collins, Jr. |
| 2009/0212127 A1 | 8/2009 | Reynolds et al. |
| 2009/0212133 A1 | 8/2009 | Collins, Jr. |
| 2009/0223513 A1 | 9/2009 | Papania et al. |
| 2010/0001090 A1 | 1/2010 | Neergaard et al. |
| 2010/0005903 A1 | 1/2010 | Beavis |
| 2010/0013352 A1 | 1/2010 | Pletner et al. |
| 2010/0044460 A1 | 2/2010 | Sauzade |
| 2010/0072301 A1 | 3/2010 | Cater |
| 2010/0072302 A1* | 3/2010 | Cater .................. B05B 1/3053 239/333 |
| 2010/0076388 A1 | 3/2010 | Cater |
| 2010/0147899 A1 | 6/2010 | Nardi |
| 2010/0186738 A1 | 7/2010 | Kobayashi et al. |
| 2010/0222752 A1 | 9/2010 | Collins, Jr. |
| 2010/0236545 A1 | 9/2010 | Kern |
| 2010/0295420 A1 | 11/2010 | Wierach |
| 2010/0326431 A1 | 12/2010 | Yu |
| 2011/0074247 A1 | 3/2011 | Hohlfeld et al. |
| 2011/0102735 A1 | 5/2011 | Gupta et al. |
| 2011/0106025 A1 | 5/2011 | Hall et al. |
| 2011/0146670 A1 | 6/2011 | Gallem et al. |
| 2011/0284579 A1 | 11/2011 | Pardes et al. |
| 2011/0293452 A1 | 12/2011 | Kim et al. |
| 2012/0017898 A1 | 1/2012 | Moller |
| 2012/0062840 A1 | 3/2012 | Ballou, Jr. et al. |
| 2012/0070467 A1 | 3/2012 | Ballou, Jr. et al. |
| 2012/0143152 A1 | 6/2012 | Hunter et al. |
| 2012/0179122 A1 | 7/2012 | Eilat et al. |
| 2012/0197219 A1 | 8/2012 | Scanlon et al. |
| 2012/0304929 A1 | 12/2012 | Ivri |
| 2013/0002095 A1 | 1/2013 | Van Der Linden |
| 2013/0017283 A1 | 1/2013 | Zemel et al. |
| 2013/0025038 A1 | 1/2013 | Frey et al. |
| 2013/0053042 A1 | 2/2013 | Tanikawa et al. |
| 2013/0079733 A1 | 3/2013 | Burt et al. |
| 2013/0118619 A1 | 5/2013 | Loth et al. |
| 2013/0140225 A1 | 6/2013 | Decock et al. |
| 2013/0150812 A1 | 6/2013 | Hunter et al. |
| 2013/0152796 A1 | 6/2013 | Pawl |
| 2013/0153677 A1 | 6/2013 | Leen et al. |
| 2013/0164436 A1 | 6/2013 | Yagi et al. |
| 2013/0172830 A1 | 7/2013 | Hunter et al. |
| 2013/0206857 A1 | 8/2013 | Ivri |
| 2013/0299607 A1 | 11/2013 | Wilkerson et al. |
| 2013/0345672 A1 | 12/2013 | Ferreri et al. |
| 2014/0088524 A1 | 3/2014 | Marx |
| 2014/0113946 A1 | 4/2014 | Abad |
| 2014/0157956 A1 | 6/2014 | Date et al. |
| 2014/0171490 A1 | 6/2014 | Gross et al. |
| 2014/0187969 A1 | 7/2014 | Hunter et al. |
| 2014/0214024 A1 | 7/2014 | Eichler |
| 2014/0224267 A1 | 8/2014 | Levitz et al. |
| 2014/0242022 A1 | 8/2014 | Vehige et al. |
| 2014/0249491 A1 | 9/2014 | Ballou, Jr. et al. |
| 2014/0257172 A1 | 9/2014 | Yalamanchili |
| 2014/0274910 A1 | 9/2014 | Cumberlidge et al. |
| 2014/0276054 A1 | 9/2014 | Hossack et al. |
| 2014/0285121 A1 | 9/2014 | Balogh et al. |
| 2014/0323931 A1 | 10/2014 | Avni |
| 2014/0336596 A1 | 11/2014 | Wochele |
| 2014/0336618 A1 | 11/2014 | Wilkerson et al. |
| 2015/0018781 A1 | 1/2015 | Rinderknect et al. |
| 2015/0035180 A1 | 2/2015 | Shen et al. |
| 2015/0036219 A1 | 2/2015 | Shen et al. |
| 2015/0040891 A1 | 2/2015 | Avni |
| 2015/0086397 A1 | 3/2015 | Ma |
| 2015/0097050 A1 | 4/2015 | Ciervo |
| 2015/0139973 A1 | 5/2015 | Steinfeld et al. |
| 2015/0144128 A1 | 5/2015 | Hijlkema et al. |
| 2015/0209174 A1 | 7/2015 | Abreu |
| 2015/0209178 A1 | 7/2015 | Blakey et al. |
| 2015/0238689 A1 | 8/2015 | Shimizu |
| 2015/0256730 A1 | 9/2015 | Shen et al. |
| 2015/0260179 A1* | 9/2015 | Hatton .................. B05B 11/007 417/395 |
| 2015/0276994 A1 | 10/2015 | Shen et al. |
| 2015/0308421 A1 | 10/2015 | Vogt |
| 2015/0328151 A1 | 11/2015 | Ballou, Jr. et al. |
| 2015/0352297 A1* | 12/2015 | Stedman ........... A61M 15/0033 128/200.14 |
| 2016/0107180 A1 | 4/2016 | Decock et al. |
| 2016/0120833 A1 | 5/2016 | Wan et al. |
| 2016/0129467 A1* | 5/2016 | Ciardella ................ B05B 17/04 222/1 |
| 2016/0199225 A1 | 7/2016 | Ivri |
| 2016/0199230 A1 | 7/2016 | Doshi et al. |
| 2016/0213866 A1 | 7/2016 | Tan |
| 2016/0263314 A1 | 9/2016 | Pardes et al. |
| 2016/0296367 A1* | 10/2016 | Ivri ...................... A61F 9/0008 |
| 2016/0354559 A1 | 12/2016 | Gavini et al. |
| 2016/0368053 A1* | 12/2016 | Hatton ............... B05B 11/1001 |
| 2017/0028626 A1 | 2/2017 | Delrot et al. |
| 2017/0136484 A1 | 5/2017 | Wilkerson et al. |
| 2017/0138357 A1 | 5/2017 | Kondo et al. |
| 2017/0151088 A1 | 6/2017 | Ballou, Jr. et al. |
| 2017/0156927 A1 | 6/2017 | Richter et al. |
| 2017/0182510 A1 | 6/2017 | Wilkerson et al. |
| 2017/0187969 A1 | 6/2017 | Kitamori et al. |
| 2017/0274159 A1 | 9/2017 | Gavini et al. |
| 2017/0344714 A1 | 11/2017 | Ballou, Jr. et al. |
| 2018/0085251 A1 | 3/2018 | Hunter et al. |
| 2018/0108275 A1 | 4/2018 | Newberry et al. |
| 2018/0116871 A1 | 5/2018 | Hunter et al. |
| 2018/0207030 A1 | 7/2018 | Ivri |
| 2018/0229247 A1* | 8/2018 | Laidler ................ B05B 1/3405 |
| 2018/0236466 A1 | 8/2018 | Laidler |
| 2018/0297053 A1 | 10/2018 | Buckland et al. |
| 2019/0053945 A1 | 2/2019 | Hunter et al. |
| 2019/0074086 A1 | 3/2019 | Ballou, Jr. et al. |
| 2019/0099071 A1 | 4/2019 | Ehrmann |
| 2019/0314195 A1 | 10/2019 | Ivri |
| 2019/0314196 A1 | 10/2019 | Ivri et al. |
| 2019/0314197 A1 | 10/2019 | Ivri et al. |
| 2019/0314198 A1 | 10/2019 | Ivri et al. |
| 2020/0022416 A1 | 1/2020 | Alarcon |
| 2020/0197218 A1 | 6/2020 | Newell et al. |
| 2020/0246182 A1 | 8/2020 | Ivri |
| 2020/0281768 A1 | 9/2020 | Quintana et al. |
| 2020/0315842 A1 | 10/2020 | Palanker et al. |
| 2020/0330267 A1 | 10/2020 | Li et al. |
| 2021/0128350 A1 | 5/2021 | Ivri et al. |

(56) References Cited

U.S. PATENT DOCUMENTS

| | | | |
|---|---|---|---|
| 2021/0220169 | A1 | 7/2021 | Ivri |
| 2021/0322209 | A1 | 10/2021 | Ivri |
| 2021/0322210 | A1 | 10/2021 | Ivri |
| 2022/0039998 | A1 | 2/2022 | Ivri |
| 2022/0125631 | A1 | 4/2022 | Tanchulev et al. |
| 2022/0160542 | A1 | 5/2022 | Palanker et al. |
| 2022/0192874 | A1 | 6/2022 | Ivri |

FOREIGN PATENT DOCUMENTS

| | | | | |
|---|---|---|---|---|
| CN | 104582647 | A | 4/2015 | |
| CN | 204813955 | U | 12/2015 | |
| CN | 107530509 | A | 1/2018 | |
| EP | 0622035 | A1 | 11/1994 | |
| EP | 0622035 | B1 | 3/1999 | |
| EP | 1493410 | A2 | 1/2005 | |
| JP | 3055480 | U | 1/1999 | |
| JP | 2007531577 | A | 11/2007 | |
| JP | 2013535250 | A | 9/2013 | |
| KR | 10-1258025 | B1 | 4/2013 | |
| KR | 10-2013-0054352 | A | 5/2013 | |
| WO | 1994020875 | A3 | 1/1995 | |
| WO | 1996000050 | A1 | 1/1996 | |
| WO | WO-9600050 | A1 * | 1/1996 | ........... A61F 9/0008 |
| WO | 2001046134 | A1 | 6/2001 | |
| WO | 2002072169 | A2 | 9/2002 | |
| WO | 2010078428 | A1 | 7/2010 | |
| WO | 2012009706 | A1 | 1/2012 | |
| WO | WO-2013076682 | A1 * | 5/2013 | ........... A61M 11/007 |
| WO | 2013090459 | A1 | 6/2013 | |
| WO | 2013090468 | A1 | 6/2013 | |
| WO | 2013155201 | A2 | 10/2013 | |
| WO | 2013158967 | A3 | 12/2013 | |
| WO | 2016115050 | A1 | 7/2016 | |
| WO | 2016164830 | A1 | 10/2016 | |
| WO | WO-2018136618 | A2 * | 7/2018 | ........... A61F 9/0008 |
| WO | 2018227190 | A1 | 12/2018 | |
| WO | 2019113483 | A1 | 6/2019 | |
| WO | 2020010116 | A1 | 1/2020 | |

OTHER PUBLICATIONS

Ali et al., "Glaucoma and Dry Eye", Ophthalmology, 2009, vol. 116, p. 1232.
Brenton, "CRUK/10/30: TRICON8—Sample collection of ovarian cancer tissues and blood for translational research from patients participating in the CR-UK/MRC ICON8 trial", 2015, online abstract.
Choi et al., "Generation of Controllable Monodispersed Sprays Using Impulse Jet and Charging Techniques", Review of Scientific Instruments, 1990, vol. 61, pp. 1689-1693.
Denion et al., "A 5-Minute Interval between Two Dilating Eye Drops Increases Their Effect", Jul. 19, 2017, Optometry and Vision Science, vol. 94, pp. 838-844.
Electronic Tutorials, "Linear Solenoid Actuator", 2016 [online]; [Retrieved on Oct. 17, 2022], Retrieved from the Internet [URL: https://www.electronics-tutorials.ws/io/io_6.html].
Elert, Glenn, "Spherical mirrors", The Physics Hypertextbook, 2021 [online]; [Retrieved on Oct. 17, 2022], Retrieved from the Internet [URL: https://physics.info/mirrors/].
Gannon, Megan, "The Best Length for Eyelashes, According to Science", Feb. 24, 2015 [online]; [Retrieved on Oct. 17, 2022], Retrieved from the Internet [URL: https://www.livescience.com/49934-optimal-length-for-eyelashes-discovered.html].

Ianchulev et al., "Pharmacodynamic profile of mydriatic agents delivered by ocular piezo-ejection microdosing compared with conventional eyedropper", 2016, Ther. Deliv., vol. 7, pp. 751-760.
Jow et al., "Design and Optimization of Printed Spiral Coils for Efficient Transcutaneous Inductive Power Transmission", IEEE Transactions on Biomedical Circuits and Systems, 2007, vol. 1, pp. 193-202.
Kent, Christopher, "Getting Meds onto the Eye, 21st Century Style", Mar. 15, 2013 [online]; [Retrieved on Aug. 27, 2019], Retrieved from the Internet [URL: https://www.reviewofophthalmology.com/article/getting-meds-onto-the-eye-21st-century-style].
Kompella et al., "ISOPT Clinical Hot Topic Panel Discussion on Ocular Drug Delivery", 2019, J. Ocul. Pharmacol. Ther., vol. 35, pp. 457-465.
Lallemand et al., "Cyclosporine A Delivery to the Eye: A Comprehensive Review of Academic and Industrial Efforts", European Journal of Pharmaceutics and Biopharmaceutics, 2017, vol. 117, pp. 14-28.
Lindblad et al., "Production of Uniform-Sized Liquid Droplets", Journal of Scientific Instruments, 1965, vol. 42, pp. 635-638.
Lux et al., "A Comparative Bioavailability Study of Three Conventional Eye Drops Versus a Single Lyophilisate", Br. J. Ophthalmol., 2003, vol. 87, pp. 436-440.
Macmillan Online Dictionary, "Stream," n.d. [online]; [Retrieved on Dec. 13, 2018]; Retrieved from the Internet [URL: https://macmillandictionary.com/dictionary/american/stream_ 1#stream_ 9].
Marx et al., "Opthalmic Squeeze Dispenser: Eliminating the Need for Additives in Multidose Preservative-Free Eyecare Formulations", 2017, Drug Development Delivery, vol. 17, pp. 40-44.
Merriam-Webster, "Clamp," 2019 [online] [Retrieved on Oct. 25, 2022], Retrieved from the Internet [URL: https://www.merriam-webster.com/dictionary/clamp].
Merriam-Webster, "Collimate," 2020 [online] [Retrieved on Oct. 17, 2022], Retrieved from the Internet [URL: https://www.merriam-webster.com/dictionary/collimated].
Merriam-Webster, "Stream," n.d. [online]; [Retrieved on Dec. 13, 2018], Retrieved from the Internet [URL: https://www.merriam-webster.com/dictionary/stream].
Murube et al., "Classification of Artificial Tears, I: Composition and Properties", Advanced Experimental Medical Biology, 1998, vol. 438, pp. 693-704.
Murube et al., "Classification of Artificial Tears, II: Additives and Commercial Formulas", Advanced Experimental Medical Biology, 1998, vol. 438, pp. 705-715.
Oxford Online Dictionary, "Stream," n.d. [online]; [Retrieved on Dec. 13, 2018]; Retrieved from the Internet [URL: https://en.oxforddictionaries.com/definition/us/stream].
Pronin et al., "Teaching an Old Drug New Tricks: Agonism, Antagonism, and Biased Signaling of Pilocarpine through M3 Muscarinic Acetylcholine Receptor", 2017, Mol. Pharmacol., vol. 92, pp. 601-612.
Vocabulary.com, "Stream," n.d. [online]; [Retrieved on Dec. 13, 2018]; Retrieved from the Internet [URL: https://www.dictionary.com/stream].
Birkhoff et al., "New Devices for Dispensing Ophthalmic Treatments May Be the Key to Managing the Life Cycles of Established Products", 2010, Drug Delivery Technology, vol. 10, pp. 16-21.
International Search Report and Written Opinion dated Jun. 5, 2020 in corresponding International Patent Application No. PCT/US2020/021504 (7 pages).
International Search Report and Written Opinion dated Mar. 29, 2021 in corresponding International Patent Application No. PCT/US2020/066169 (7 pages).

* cited by examiner

VENTED MULTI-DOSE OCULAR FLUID DELIVERY SYSTEM

CROSS REFERENCE TO RELATED APPLICATIONS

This application claims the benefit of U.S. provisional patent application 62/951,903, filed on Dec. 20, 2019, and hereby incorporated by reference in its entirety.

This application claims the benefit of U.S. provisional patent application 63/049,582, filed on Jul. 8, 2020, and hereby incorporated by reference in its entirety.

This application claims the benefit of U.S. provisional patent application 63/011,800, filed on Apr. 17, 2020, and hereby incorporated by reference in its entirety.

This application claims the benefit of U.S. provisional patent application 63/049,110, filed on Jul. 7, 2020, and hereby incorporated by reference in its entirety.

This application is a continuation in part of U.S. application Ser. No. 16/811,879, filed on Mar. 6, 2020, and hereby incorporated by reference in its entirety.

FIELD OF THE INVENTION

This invention relates to topical ocular delivery of ophthalmic medications.

BACKGROUND

Currently, pharmaceutical fluids are typically delivered to the eye surface using a drop bottle. This method has multiple drawbacks: (1) Patients cannot aim well and often miss the eye; (2) Volume of a drop from a bottle is not well-defined and is too large (on the order of 50 µL) for the tear film on the cornea to absorb it—the tear film can hold no more than about 7 µL; (3) Very often patients blink during the drop delivery, so that part of the drop lands on the eyelid, and the rest is wiped off the cornea.

SUMMARY

We have developed a device that addresses these problems by (1) delivery of a precise amount of fluid; (2) with a micro-dose that the tear film can hold (<10 uL); (3) deliver it within the blink time (~100 ms), and (4) using an optical aiming onto the cornea for precise self-administration.

For convenient aiming, the fluid ejector should be placed close to the eye, but not touch the eyelashes or eyebrow. Therefore, with reference to FIG. 1, the device 102 should be in the range of approximately L=1-10 cm from the eye, or more optimally 2-6 cm. On this figure, 102 is the fluid ejector, 104 is the emitted fluid stream and 106 is the patient's eye.

The cornea is about D=12 mm in diameter, i.e. 6 mm in radius. To ensure that the fluid is delivered approximately to the middle of the cornea, the jet 104 should not deflect under gravity by more than about half the cornea radius, i.e. no more than about h=3 mm. As shown in FIG. 1, vertical deflection h of the projectile ejected horizontally with velocity v over a distance L is: $h = g*L/(2 v^2)$. To ensure that vertical deflection does not exceed h, horizontal jet velocity should exceed $v = L*(g/2 h)^{0.5}$. For L=5 cm, g=9.8 m/s², h=3 mm, we obtain v=2 m/s. For L=5 cm and h=1 mm, velocity should be about v=3.6 m/s, and for L=10 cm, h=1 mm, velocity v=7.2 m/s. Therefore overall, jet velocity should be in the range of about 1-10 m/s, and more optimally 2-4 m/s. Velocities much higher than those may cause discomfort to the patient and even damage to the cornea.

The stream of fluid will reach the eye within a few milliseconds from the moment of dispensing (t=L/v, in the range of 1-100 ms). As soon as the fluid will touch the cornea, it will trigger the blink reflex, which typically takes about T=100 ms. To prevent the drug being blocked by the eyelid, the fluid should be delivered before the eye closure. For the required volume V to be delivered within the time T with the jet velocity v, the jet cross-sectional area should be $S=V/(T*v)$. Since for a round aperture, $S=\pi*d^2/4$, its diameter $d=(4V/(\pi T*v))^{0.5}$. For example, for v=2 m/s, T=100 ms, V=10 µL, we obtain d=250 µm. For v=1 m/s, d=350 µm, and for v=7 m/s, d=130 µm.

Therefore, the aperture diameter of the ejector should be in the range of approximately 200-600 µm, and more optimally 400-550 µm. Alternatively, several apertures could be used to produce several parallel streams for faster delivery.

Another key attribute of the system is the prevention of microbial ingress to the contained liquid during storage or use. As with any closed system, as liquid is ejected, air should be introduced to replace the ejected volume and thereby balance the pressure (venting). To preclude microbial ingress, the air is introduced via a special inlet preferably having a 0.2 um filter. Ideally, the device should operate such that liquid is ejected through the aperture any time it is opened, thereby preventing the air ingress through it.

An exemplary embodiment is an arrangement for storing and discharging liquid droplets having a housing including a chamber for holding liquid therein and having an intake port connected to an ampoule containing pharmaceutical fluid to be dispensed. The chamber includes a dispensing aperture plate which defines a frontal closure to the chamber and includes an aperture opening therein through which the liquid is discharged forwardly of the housing. The chamber further includes a vibrating membrane secured to the housing in pressure transmitting relation with the liquid in the chamber. The vibrating membrane is formed with a needle which protrudes from its center and extends to the aperture in the opposite side of the chamber, said needle closes the aperture to prevent outflow of liquid from the chamber and ingress of bacteria.

An electromagnetic transducer is attached to the housing, and when energized, pulls the membrane rearward against a spring in the chamber. When the electromagnetic transducer is turned off, the spring returns the membrane to its original position with the valve closed. When the electromagnetic transducer is energized with pulsatile or alternating current, the membrane is consequently oscillated, which in turn generates pressure on the liquid. At the correct frequencies, the pressure is sufficient to eject a stream of liquid from the aperture.

Typical range of frequencies is in a range of 10 Hz to 500 Hz, more optimally 50 to 200 Hz. The diameter of the nozzle, velocity of the fluid ejection, and duration of the electromagnetic burst are preferably optimized to deliver the required amount of fluid within the required amount of time, as described above. Preferably the actuation pulse duration is 250 ms or less, and more preferably it is 100 ms or less. Here 'actuation pulse duration' refers to the length of time the electromagnetic transducer is energized so as to pull the needle out of the aperture in a single actuation pulse.

Other kinds of transducer can also be used to drive fluid ejection in this configuration, such as a coin vibration motor.

DETAILED DESCRIPTION

Figure 1:
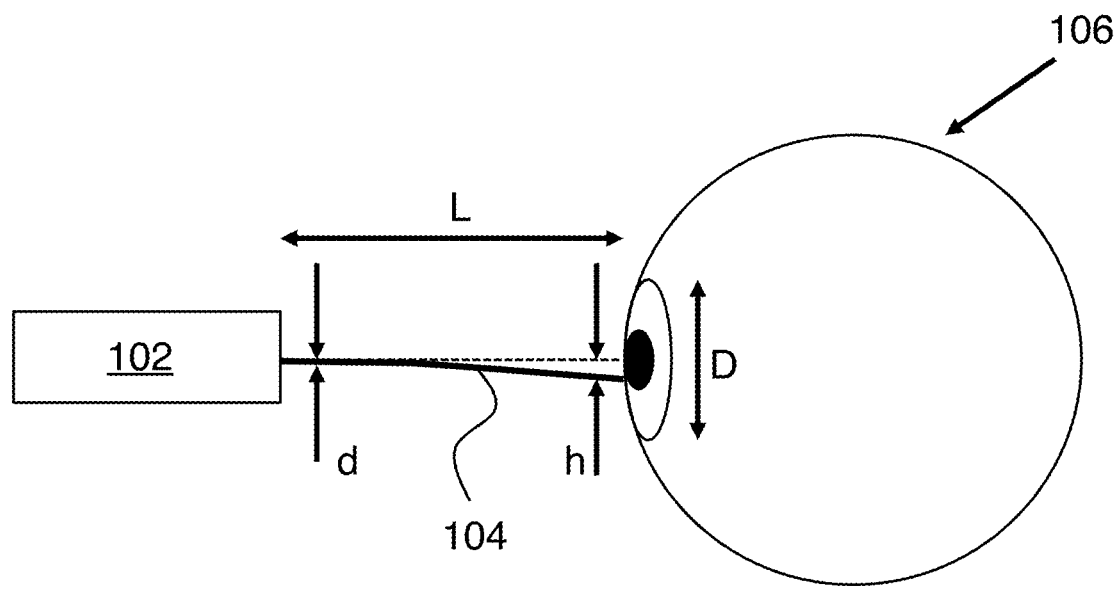
FIG. 1 shows geometry for delivering fluid to an eye of a patient.
Figure 2:
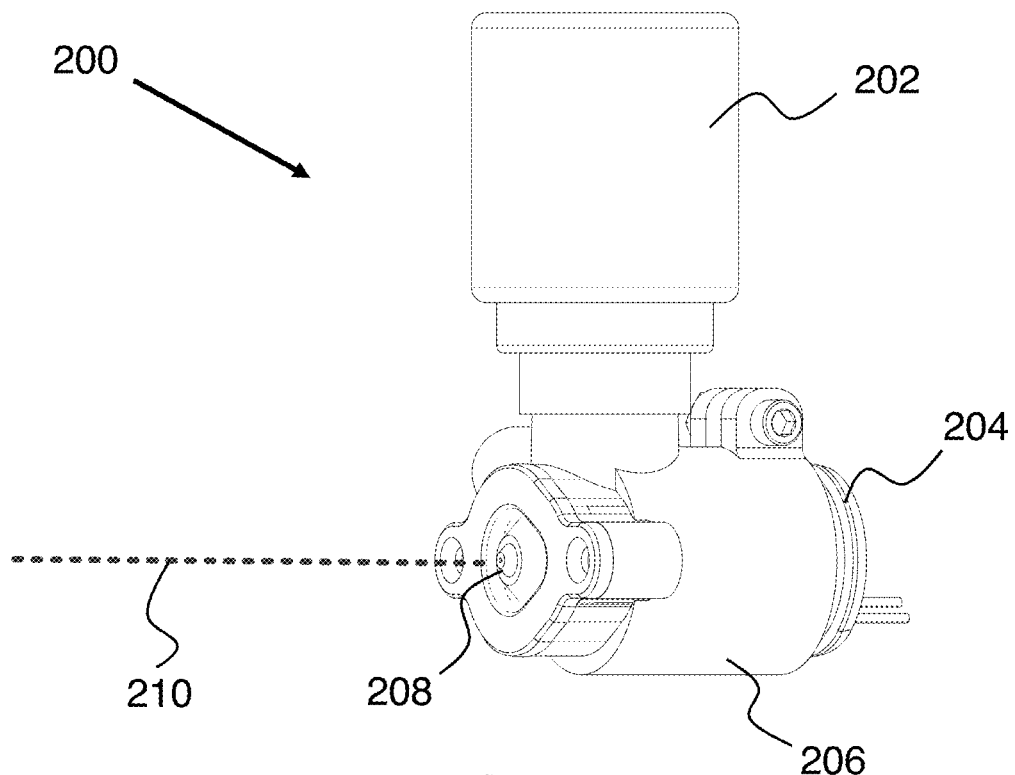
FIG. 2 is an exterior view of an exemplary embodiment of the invention.

FIG. 2 shows a perspective view of a first embodiment of the liquid ejection unit. The fluid ejection unit 200, is specifically but not exclusively suitable for use in delivering preservative-free pharmaceutical liquid to the surface of the eye. Liquid ejection device 200 comprises a thermoplastic body 206 formed with a liquid chamber and connected to a fluid supply ampule 202. The ejection unit includes nozzle 208 through which liquid 210 is dispensed as will explained in greater detail below.

Figure 3A:
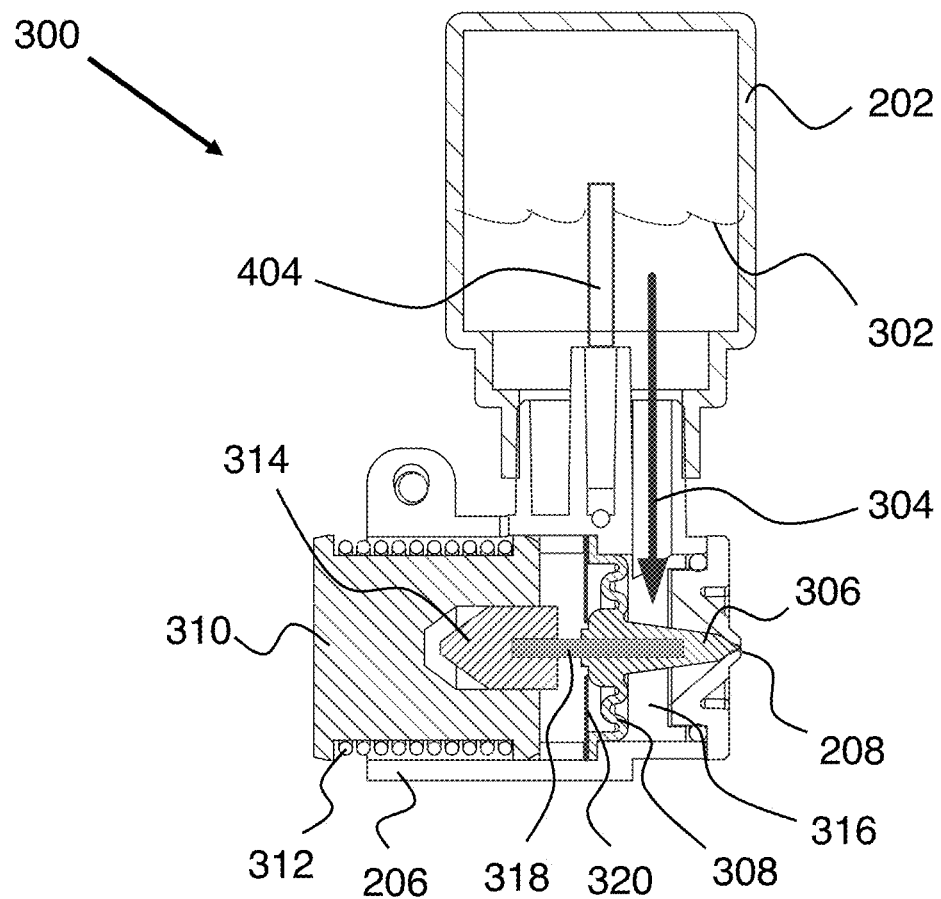
FIG. 3A is a cross section view of a first embodiment of the invention.

FIG. 3A illustrates a cross-sectional view of the fluid ejection device. As mentioned earlier the fluid ejection device comprises a thermoplastic body 206 defining a chamber 316 connected to the fluid supply ampule 202 containing a fluid 302. The fluid ejection device includes a nozzle 208 through which liquid is ejected. The device further includes a membrane 308 at the opposite end of the chamber from the nozzle. Membrane 308 includes an integral needle 306 such that they are one component. The needle 306 and the membrane 308 are connected to an electromagnetic transducer 310 via a link member 318. Upon application of an electrical pulse to the electromagnetic transducer 310, electric current flows through the coil 312 and a magnetic force is developed which pulls plunger 314 backward against a spring 320.

On FIG. 3A, 304 shows the direction of fluid flow from ampule 202 to chamber 316. Vent tube 404 is described in greater detail below.

Figure 3B:
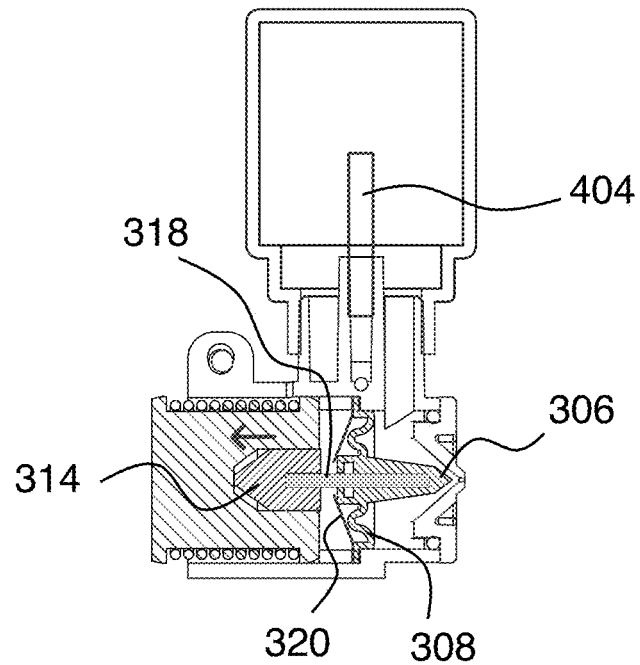
FIGS. 3B-C show operation of the embodiment of FIG. 3A.
Figure 3C:
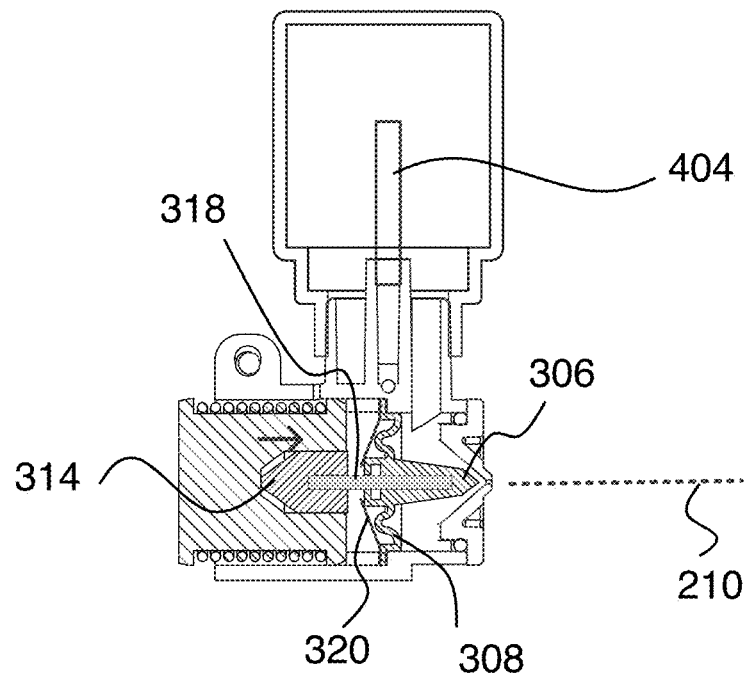

FIG. 3B shows the device of FIG. 3A following application of an electrical pulse to electromagnetic transducer 310. It can be seen that as a result from the magnetic force, plunger 314 is pulled into the electromagnetic transducer in the direction indicated by the arrow. Membrane 308 is connected to plunger 314 by linkage member 318 and is also pulled back. FIG. 3C shows the situation when the electromagnetic transducer 310 is de-energized. Here the spring 320 pushes the membrane 308 back to its original position, so the valve is closed and the chamber is hermetically sealed and prevents microbial ingress.

When the electromagnetic transducer 310 is energized with a pulsatile or alternating (AC) current, the oscillating membrane generates pressure in liquid resulting in a stream ejected from the aperture. Typically, the operating frequency is from 10 to 500 Hz and more specifically from 50 to 200 Hz. In an embodiment, the membrane 308 is made of silicon having hardness durometer between 50-70 (shore A), and the displacement of plunger 314 is about 200 um. Since the flow is produced only in the outward direction, it prevents microbial ingress even when the valve is open.

Figure 4A:
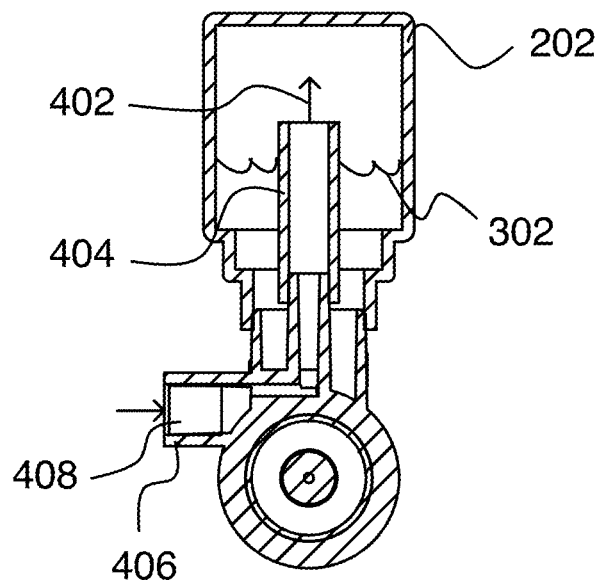
FIGS. 4A-B show an example of venting.
Figure 4B:
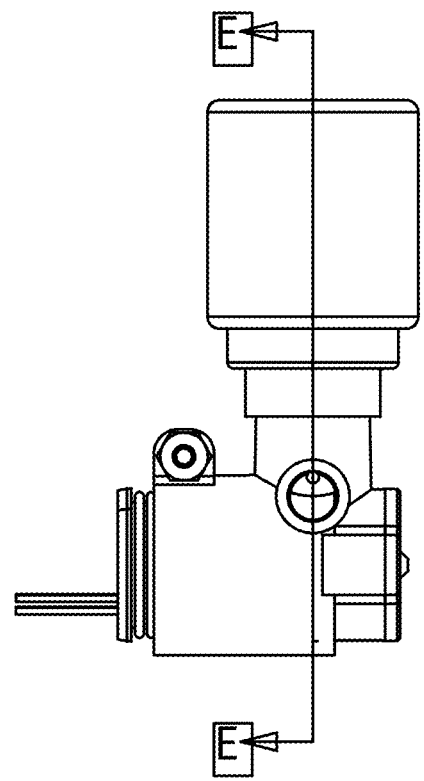

In the example of FIGS. 4A-B, the liquid ejection device includes a venting arrangement to equalize the pressure inside the ampule 202 with the ambient atmospheric pressure. Here FIG. 4A is a cross section view along line E-E of FIG. 4B.

The venting system of this example includes an air inlet vent tube 404 that is extended beyond the liquid level of fluid 302 in the ampoule 202. It should be noted that the vent tube 404 is above the liquid level in any orientation of the device of FIGS. 4A-B. Vent tube 404 is connected to venting outlet 406, which is open to the atmosphere. In one embodiment, a filter 408 is placed in the venting outlet 406 such that the vented air flowing to the ampoule is filtered to prevent penetration of potential airborne contamination, such as microbes. Filter 408 will filter away particles with size >1 μm (more preferably >0.5 μm, still more preferably >0.2 μm). In this way the system can be isolated from microbial contamination, even though air 402 enters the ampule 202 as fluid is emitted.

Figure 5:
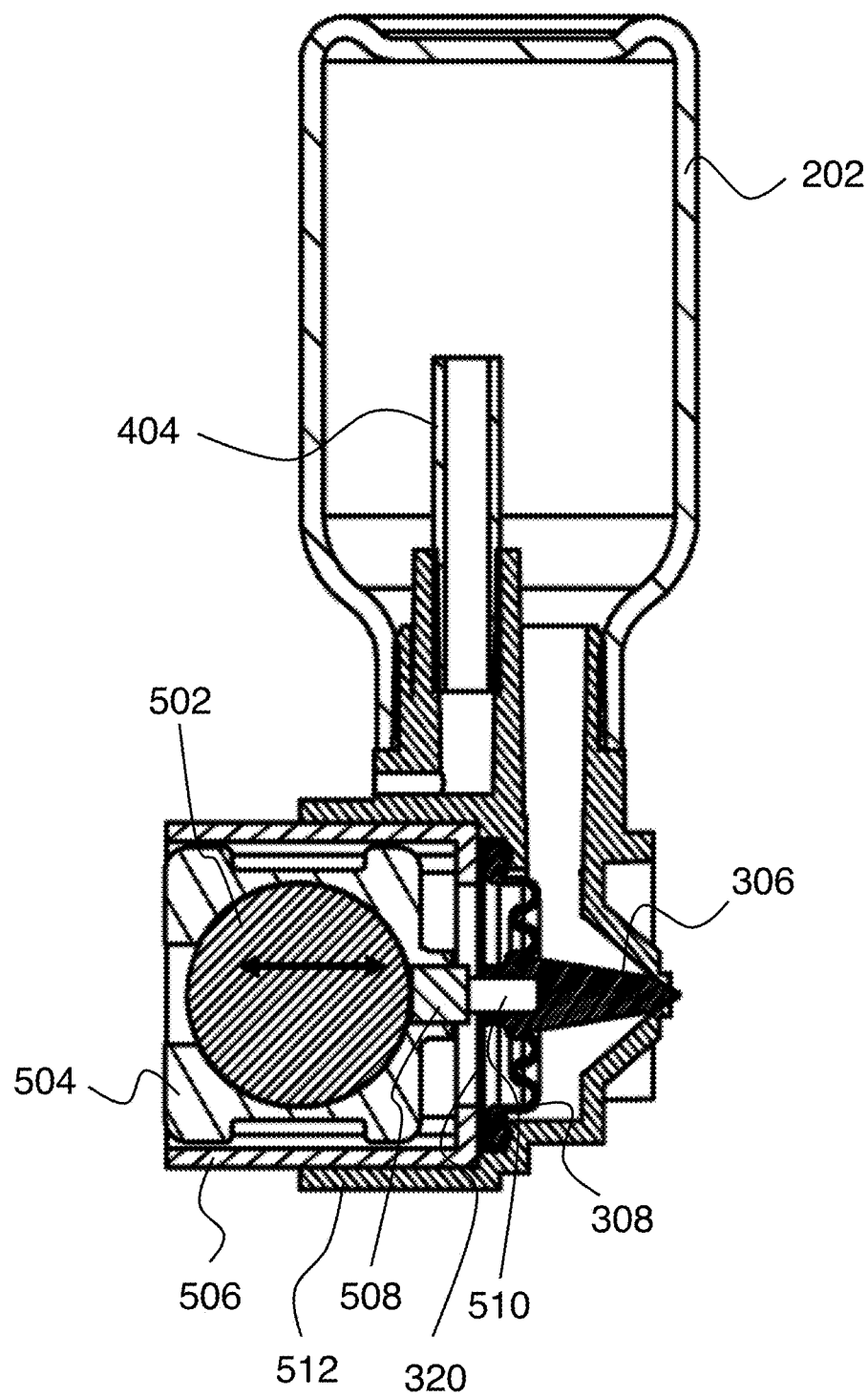
FIG. 5 is a cross section view of a second embodiment of the invention.

In the preceding examples, diaphragm 308 is driven with a solenoid. In the example of FIG. 5, the diaphragm is driven by using a coin vibration motor. More specifically, 306 is a needle connected to a diaphragm 308 as described above. This assembly is overmolded with a magnetic steel pin 510. 502 is a coin vibrator motor (e.g., JINLONG MACHINERY & ELECTRONICS CO., LTD. model #C1026B002F). 504 is a plastic molded component which holds the motor 502 such that it can slide along rails (i.e., it is a motor holder). 506 is a plastic molded component that provides the above-mentioned rail guides for motor holder 504 to slide within. 510 is a magnetic steel pin which is molded into the membrane/needle assembly (308/306). 512 is the housing that holds all the components together.

Needle 306 normally seals the aperture (i.e., the aperture is sealed except when fluid is being emitted), as described in greater detail above. A coin vibration motor has an eccentric weight off its axis of rotation (the axis of rotation is perpendicular to the plane of FIG. 5). Because the weight is off axis, as the motor rotates the unbalanced weight causes the motor to vibrate primarily in the plane of FIG. 5. By placing the coin vibration motor 502 in a plastic motor holder 504 which fits into corresponding rails (in member 506), the coin vibration motor is constrained so it can only move linearly (e.g., left to right on FIG. 5). As a result of this physical constraint, when the motor rotates, it is only allowed to oscillate left to right, rather than to vibrate in a plane. The coin vibration motor is coupled to the diaphragm 308, consequently as the motor oscillates left to right, the diaphragm is also vibrated left to right. The ejected fluid stream is generated in the same manner as described above—i.e., the needle 306 moves back and forth in the aperture to eject the liquid.

In an alternative embodiment, the coin vibration motor 502 can be coupled to the diaphragm via an optional magnet 508. Magnet 508 is fixed to motor holder 504 which is also affixed to the coin vibration motor 502. When the magnet 508 is close to the magnetic steel pin 510, the two latch together and the motor is thereby coupled to the diaphragm. This is an advantageous assembly feature, because the motor can be easily added to the system without the need for tight tolerances and the motor can be added at several different steps of the assembly process.

The example of FIG. 5 includes a disk-shaped spring 320. The spring is slightly deformed out of plane during assembly which serves to transmit force to needle 306. This force or load keeps the needle 306 pressed up against the orifice to close the flow path. Without the spring, the force required to push the needle open is very low and the device will readily leak. Additionally, the spring has a spring constant which is important for ensuring the correct frequency and amplitude of oscillation of the needle when the motor is energized. Also important is that without the spring it is only the stiffness of the diaphragm 308 which applies a load to keep the needle 306 in the closed position. The diaphragm can be made of an elastomer. For most elastomers mechanical properties vary significantly even with modest temperature changes. With the spring 320, a significant portion of the load applied to the needle 306 comes from the spring 320, not the diaphragm 308. Because the mechanical properties of spring steel (e.g., the material of the spring 320) are far more constant for the same temperature change, adding the spring makes the system performance more consistent.

Figure 6:
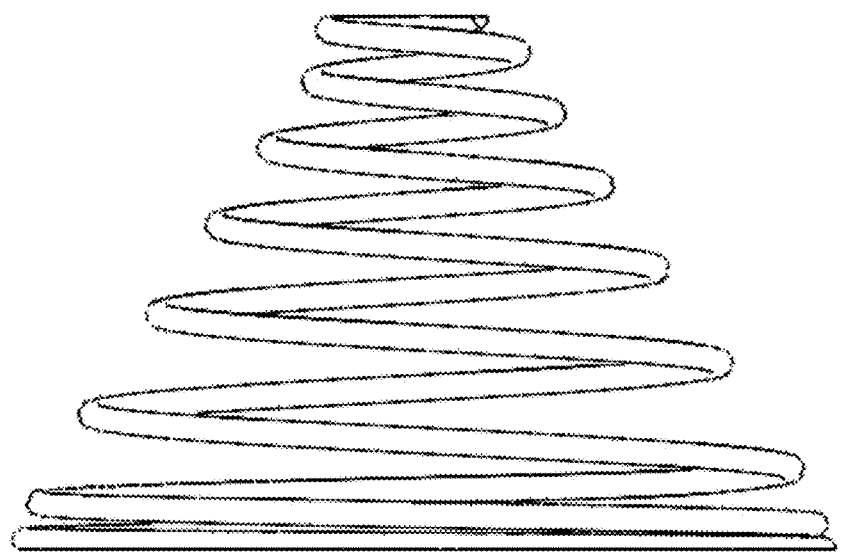
FIG. 6 shows a conical spring.

In an alternative embodiment, the disc spring 320 of FIG. 5 is replaced with a conical spring. A conical spring is similar to a conventional compression spring made of wire, but instead of being wound with a constant diameter, the diameter gets progressively smaller so that the spring has the shape of a cone, not a cylinder. See FIG. 6. When a conical spring is fully compressed, the coils nest within each other so the spring can become flat, only being as thick as the diameter of the wire it is wound from. Thus a fully compressed conical spring can fit in a similar form factor as the disc spring 320 of FIG. 5 and can serve the same function. The conical spring is cheaper, and it is easier to get a wide range of spring constants and operating deflections compared to the disc spring, so it is a feature of presently preferred embodiments.

The tip of needle 306 and/or the aperture it engages with can include an anti-microbial material.

The invention claimed is:

1. An apparatus for delivering a fluid to an eye of a patient, the apparatus comprising:
   a fluid package comprising a reservoir configured to hold a fluid, an aperture, and a needle configured to seal the aperture when fluid is not being ejected through the aperture;
   wherein the fluid package comprises a resilient diaphragm configured to provide a mechanical force to hold a tip of the needle in engagement with the aperture when fluid is not being ejected through the aperture;
   wherein the resilient diaphragm is connected to the needle;
   an actuator configured to eject the fluid through the aperture by providing a mechanical vibration at least to the needle; and
   a vent configured to allow air to enter the reservoir as fluid leaves the reservoir.

2. The apparatus of claim 1, further comprising a particle filter configured to remove particles larger than 0.2 μm from air that enters the reservoir via the vent.

3. The apparatus of claim 1, wherein the actuator includes an electromagnetic solenoid.

4. The apparatus of claim 1, wherein the actuator includes a coin vibration motor.

5. The apparatus of claim 1, wherein the fluid package comprises a resilient spring configured to provide an additional mechanical force to hold the tip of the needle in engagement with the aperture when fluid is not being ejected through the aperture.

6. The apparatus of claim 1, wherein the apparatus is configured to deliver a dose volume of 10 μl or less.

7. The apparatus of claim 1, wherein a diameter of the aperture is in a range between 200 μm and 600 μm.

8. The apparatus of claim 1, wherein a velocity of fluid ejected from the aperture is in a range from 1 m/s to 10 m/s.

9. The apparatus of claim 1, wherein an actuation pulse duration is 250 ms or less.

10. The apparatus of claim 1, wherein a repetition rate of actuation pulses is in a range from 10 Hz to 500 Hz.

11. The apparatus of claim 1, wherein the needle has a tip that engages with the aperture, and wherein the tip comprises an anti-microbial material.

12. The apparatus of claim 1, wherein the aperture comprises an anti-microbial material.

13. The apparatus of claim 1, wherein the aperture is in a front wall of the reservoir and wherein the diaphragm is in a rear wall of the reservoir.

* * * * *